(12) United States Patent
Bonrath et al.

(10) Patent No.: US 12,258,311 B2
(45) Date of Patent: Mar. 25, 2025

(54) DEHYDROGENATION PROCESS

(71) Applicant: DSM IP Assets B.V., Heerlen (NL)

(72) Inventors: Werner Bonrath, Kaiseraugst (CH); Marc-André Mueller, Kaiseraugst (CH); Bettina Wuestenberg, Kaiseraugst (CH); Viktor Zimmermann, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 444 days.

(21) Appl. No.: 17/788,237

(22) PCT Filed: Dec. 15, 2020

(86) PCT No.: PCT/EP2020/086170
§ 371 (c)(1),
(2) Date: Jun. 22, 2022

(87) PCT Pub. No.: WO2021/130057
PCT Pub. Date: Jul. 1, 2021

(65) Prior Publication Data
US 2023/0068017 A1 Mar. 2, 2023

(30) Foreign Application Priority Data
Dec. 23, 2019 (EP) .................................... 19219361

(51) Int. Cl.
*C07C 47/225* (2006.01)
*C07C 45/00* (2006.01)

(52) U.S. Cl.
CPC .......... *C07C 47/225* (2013.01); *C07C 45/002* (2013.01); *C07C 2601/16* (2017.05)

(58) Field of Classification Search
CPC ........................... C07C 47/225; C07C 45/002
See application file for complete search history.

(56) References Cited

U.S. PATENT DOCUMENTS

2014/0323770 A1    10/2014    Schaub et al.

FOREIGN PATENT DOCUMENTS

| CN | 1277960 | 12/2000 |
|---|---|---|
| DE | 1 254 613 | 11/1967 |

OTHER PUBLICATIONS

International Search Report for PCT/EP2020/086170, dated Mar. 18, 2021, 3 pages.
Written Opinion of the ISA for PCT/EP2020/086170, dated Mar. 18, 2021, 5 pages.
Examination Report under sections 12 & 13 of the Patents Act, 1970 and the Patents Rules 2003, IN Application No. 202217029120, Feb. 27, 2024.

*Primary Examiner* — Sikarl A Witherspoon
(74) *Attorney, Agent, or Firm* — NIXON & VANDERHYE P.C.

(57) ABSTRACT

The present invention relates to a new compound and the dehydrogenation of that compound to produce retinal.

14 Claims, No Drawings

DEHYDROGENATION PROCESS

This application is the U.S. national phase of International Application No. PCT/EP2020/086170 filed Dec. 15, 2020 which designated the U.S. and claims priority to EP 19219361.3 filed Dec. 23, 2019, the entire contents of each of which are hereby incorporated by reference.

The present invention relates to a new compound, which is useful in the process of production of retinal (by dehydrogenation).

Retinal is an important compound, which can be used as such or it can be used to produce other derivatives of vitamin A (such as i.e. esters).

Due to its importance, there is always a need for a new and improved process to obtain retinal.

The goal of the present invention was to find a new and improved process to obtain retinal.

It was found that the newly found process allows to introduce the two double in one step under mild reaction conditions.

The new process uses the compound of formula (I)

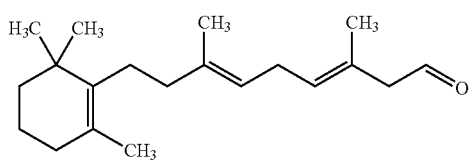
(I)

as starting material.

The compound of formula (I) can be in any of the 4 possible isomeric configurations.

The compound of formula (I) is a new compound.

Therefore, the present invention relates to the compound of formula (I)

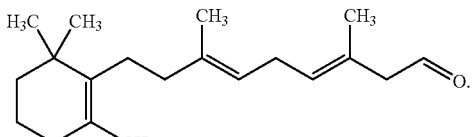
(I)

The compound of formula (I) can be produced easily by processes known from the prior art. The synthesis of the compound of formula (I) is disclosed below.

As stated above the compound of formula (I) is a very suitable compound in the synthesis of retinal, which is the compound of formula (II)

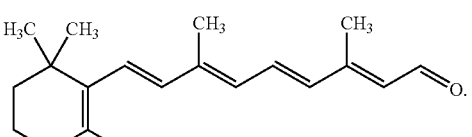
(II)

As for the compound of formula (I), the compound of formula (II) can be in any isomeric configuration.

The new dehydrogenation process according to the present invention allows to introduce two double bonds in one step.

Therefore, the present invention also relates to the dehydrogenation (DH) of the following compound of formula (I)

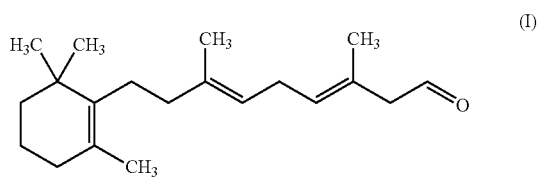 [SMILES: CC1=C(CC/C(C)=C/C/C=C(\C)CC=O)C(C)(C)CCC1]
(I)

to the compound of formula (II)

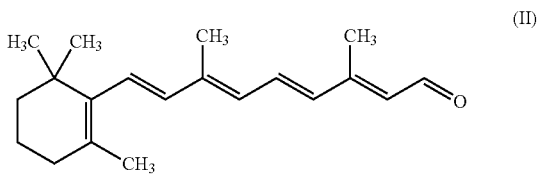 [SMILES: CC1=C(/C=C/C(C)=C/C=C/C(C)=C/C=O)C(C)(C)CCC1]
(II)

in the presence of at least one oxidative reactant of formula (III)

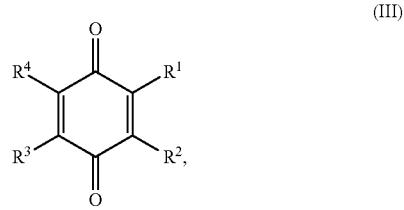
(III)

wherein
$R^1$ is CN, Cl or F,
$R^2$ is CN, Cl or F,
$R^3$ is H, $CH_3$, Cl or F, and
$R^4$ is H, $CH_3$, Cl or F.

Preferred oxidative reactants of formula (III) are those of the following formula (IIIa), (IIIb) and (IIIc):

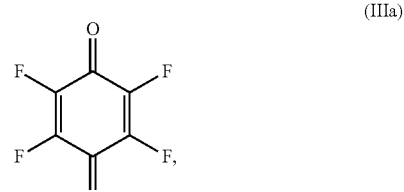
(IIIa)

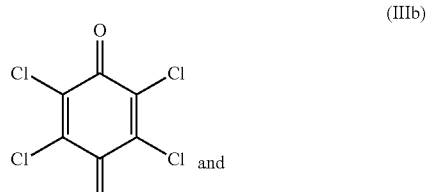
(IIIb)

and

-continued

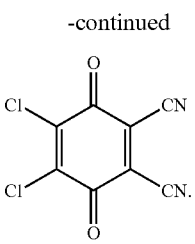
(IIIc)

Very preferred is the compound of formula (IIIc).

Therefore, the present invention relates to a dehydrogenation (DH1), which is dehydrogenation (DH), wherein the oxidative reactant is chosen from the group consisting of the compounds of formula (IIIa), (IIIb) and (IIIc)

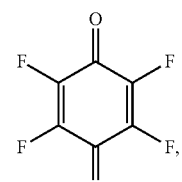
(IIIa)

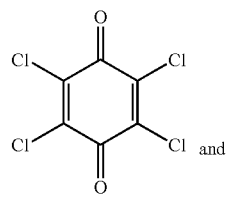
(IIIb)

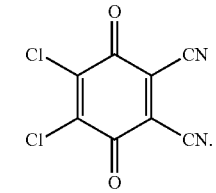
(IIIc)

Therefore, the present invention relates to a dehydrogenation (DH1), which is dehydrogenation (DH), wherein the oxidative reactant is the compound of formula (IIIc)

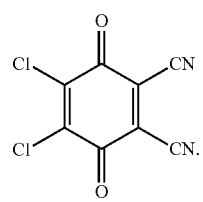
(IIIc)

The amount of the oxidative reactant of formula (III) used in the process according to the present invention can vary. The amount of the oxidative reactant of formula (III) usually goes from 0.5 mol-equivalent up to 5 mol-equivalent (in relation to compound of formula (I)). Preferably from 0.5 to 3 mol-equivalent (in relation to compound of formula (I)).

Therefore, the present invention relates to a dehydrogenation (DH2), which is dehydrogenation (DH) or (DH1), wherein the amount of the oxidative reactant of formula (III) goes from 0.5 mol-equivalent up to 5 mol-equivalent (in relation to compound of formula (I)).

Therefore, the present invention relates to a dehydrogenation (DH2'), which is dehydrogenation (DH) or (DH1), wherein the amount of the oxidative reactant of formula (III) goes from 0.5 mol-equivalent up to 3 mol-equivalent (in relation to compound of formula (I)).

The process according to the present invention can also be carried out in the presence of at least one additive compound. This additive compound is usually chosen from the group consisting of triethanolamine, pyridine, butylhydroxyltoluene, hydroquinone and triethoxyamine.

The additive compound(s) is (are) added in amount of 0.001-1 mol-equivalent (in relation to compound of formula (I)), preferably 0.003-1 mol-equivalent (in relation to compound of formula (I)).

Therefore, the present invention relates to a dehydrogenation (DH3), which is dehydrogenation (DH), (DH1), (DH2) or (DH2'), wherein the process is carried out in the presence of at least one additive compound.

Therefore, the present invention relates to a dehydrogenation (DH3'), which is dehydrogenation (DH), (DH1), (DH2) or (DH2'), wherein the additive compound is chosen from the group consisting of triethanolamine, pyridine, butylhydroxyltoluene, hydroquinone and triethoxyamine.

Therefore, the present invention relates to a dehydrogenation (DH3"), which is dehydrogenation (DH), (DH1), (DH2) or (DH2'), wherein the additive compound is added in amount of 0.001-1 mol-equivalent (in relation to compound of formula (I)).

Therefore, the present invention relates to a dehydrogenation (DH3'''), which is dehydrogenation (DH), (DH1), (DH2) or (DH2'), wherein the additive compound is added in amount of 0.003-1 mol-equivalent (in relation to compound of formula (I)).

The reaction is usually carried out in an inert solvent. The solvent is usually an aprotic solvent such as aromatic hydrocarbon (i.e. benzene or toluene), ethyl acetate, tetrahydrofuran (THF), 2-methyltetrahydrofuran or 1,4-dioxane.

Therefore, the present invention relates to a dehydrogenation (DH4), which is dehydrogenation (DH), (DH1), (DH2), (DH2'), (DH3), (DH3'), (DH3") or (DH3'''), wherein the process is carried out in the presence of at least one inert solvent.

Therefore, the present invention relates to a dehydrogenation (DH4'), which is dehydrogenation (DH4), wherein the solvent is a protic solvent.

Therefore, the present invention relates to a dehydrogenation (DH4"), which is dehydrogenation (DH4), wherein the solvent is chosen from the group consisting of aromatic hydrocarbon (i.e. benzene or toluene), ethyl acetate, THF, 2-methyltetrahydrofuran or 1,4-dioxane.

The process according to the present is usually carried out at elevated temperatures. Usually the process according to the present invention is carried out at a temperature of from 0° C.-150° C., preferably from 30° C.-150° C., more preferred from 60° C.-150° C.

Therefore, the present invention relates to a dehydrogenation (DH5), which is dehydrogenation (DH), (DH1), (DH2), (DH2'), (DH3), (DH3'), (DH3"), (DH3'''), (DH4), (DH4') or (DH4"), wherein the process is carried out at a temperature of from 0° C.-150° C.

Therefore, the present invention relates to a dehydrogenation (DH5'), which is dehydrogenation (DH), (DH1), (DH2), (DH2'), (DH3), (DH3'), (DH3"), (DH3'''), (DH4), (DH4') or (DH4"), wherein the process is carried out at a temperature of from 30° C.-150° C.

Therefore, the present invention relates to a dehydrogenation (DH5"), which is dehydrogenation (DH), (DH1), (DH2), (DH2'), (DH3), (DH3'), (DH3"), (DH3'''), (DH4), (DH4') or (DH4"), wherein the process is carried out at a temperature of from 60° C.-150° C.

As stated above the new compound of formula (I) can be produced by using process known from the prior art.

A preferred way to produce the compound of formula (I) is the following:

The compound of formula (IV) is oxidized to the compound of formula (I):

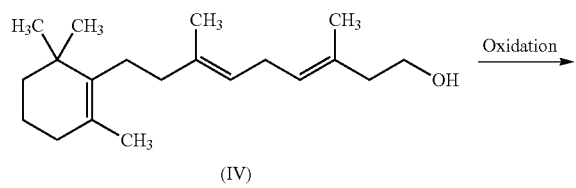

(IV)

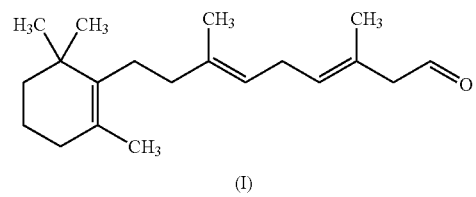

(I)

The same reaction conditions as in J. M. Hoover, S. S. Stahl, J. Am. Chem. Soc., 2011, 133, 16901-16910 are used.

The compound of formula (IV) can be obtain according to the following reaction scheme:

The following example serve to illustrate the invention. The temperature is given in ° C. and all percentages are related to the weight.

EXAMPLES

Example 1

(3E,6E)-3,7-dimethyl-9-(2,6,6-trimethylcyclohex-1-en-1-yl)nona-3,6-dienal (88 mg, 0.3 mmol; 1.0 eq), triethanolamine (3.1 mg, 0.02 mmol, 0.07 eq) and dry toluene (4.0 mL) were placed in a dried two necked round bottom flask equipped with a magnetic stirrer and condenser under an argon atmosphere. Solution of DDQ (71 mg, 0.3 mmol, 1.0 eq), in 1.0 mL dry toluene was added. The reaction was stirred at room temperature for 24 h. The reaction mixture was heated to 90° C. and a solution of DDQ (73 mg, 0.3 mmol, 1.0 eq), in 1.0 mL dry toluene was added. The reaction was stirred at 90° C. for 30 min. Subsequently cooled to room temperature and filtered over a glass fibre filter. All volatiles were evaporated under reduced pressure (40° C., 5 mbar) to obtain the product as dark red oil.

The invention claimed is:
1. A compound of formula (I):

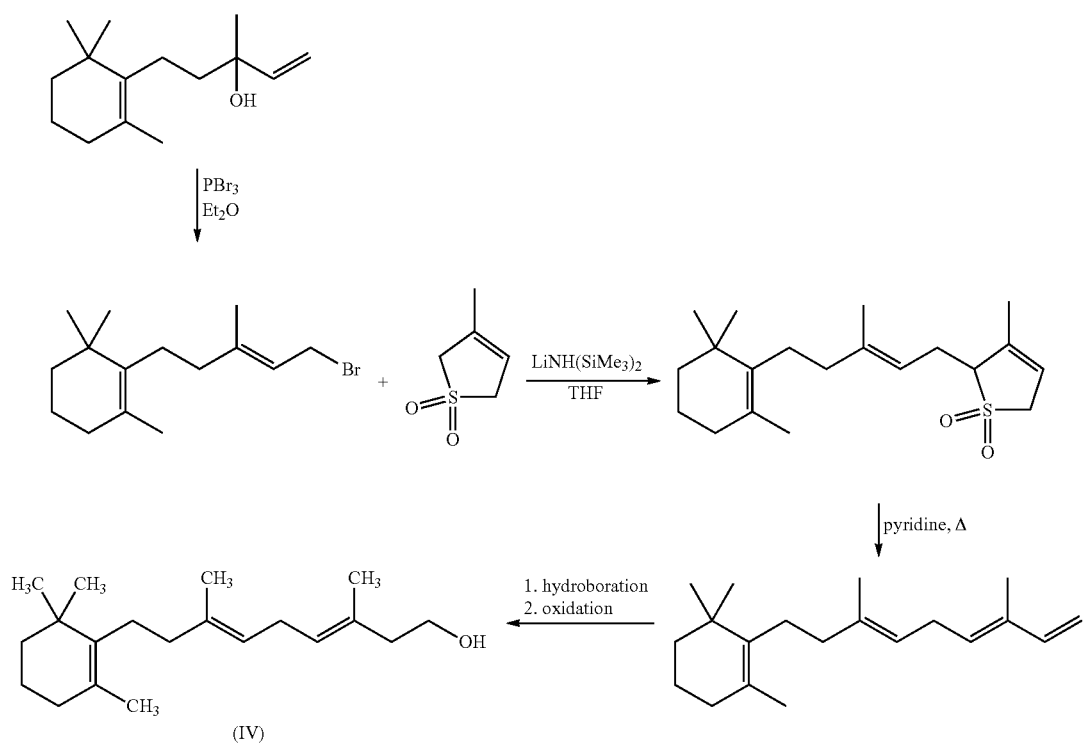

2. A dehydrogenation process which comprises conducting dehydrogenation of the compound of formula (I):

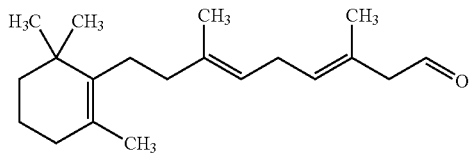

to the compound of formula (II):

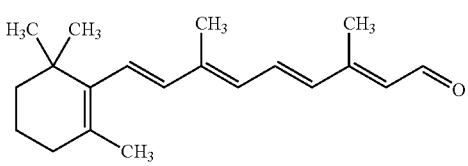

in the presence of at least one oxidative reactant of formula (III):

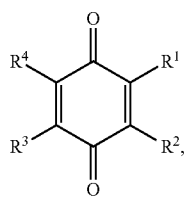

wherein
$R^1$ is CN, Cl or F,
$R^2$ is CN, Cl or F,
$R^3$ is H, $CH_3$, Cl or F, and
$R^4$ is H, $CH_3$, Cl or F.

3. The dehydrogenation process according to claim 2, wherein the at least one oxidative reactant of formula (III) is selected from the group consisting of the compounds of formula (IIIa), (IIIb) and (IIIc):

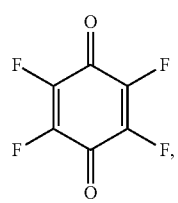

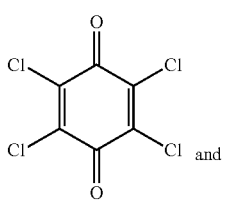

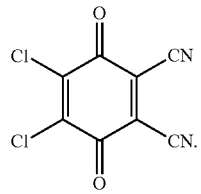

4. The dehydrogenation process according to claim 2, wherein the at least one oxidative reactant is the compound of formula (IIIc):

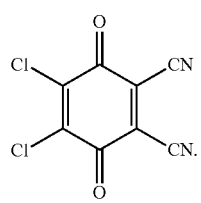

5. The dehydrogenation process according to claim 2, wherein the at least one oxidative reactant of formula (III) is present in an amount from 0.5 mol-equivalent to 5 mol-equivalent in relation to compound of formula (I).

6. The dehydrogenation process according to claim 2, wherein the at least one oxidative reactant of formula (III) is present in an amount from 0.5 mol-equivalent to 3 mol-equivalent in relation to the compound of formula (I).

7. The dehydrogenation process according to claim 2, wherein the process is carried out in the presence of at least one additive compound.

8. The dehydrogenation process according to claim 7, wherein the at least one additive compound is selected from the group consisting of triethanolamine, pyridine, butylhydroxyltoluene, hydroquinone and triethoxyamine.

9. The dehydrogenation process according to claim 7, wherein the at least one additive compound is present in amount of 0.001-1 mol-equivalent in relation to the compound of formula (I).

10. The dehydrogenation process according to claim 7, wherein the at least one additive compound is present in amount of 0.003-1 mol-equivalent in relation to the compound of formula (I).

11. The dehydrogenation process according to claim 2, wherein the process is carried out in the presence of at least one inert solvent.

12. The dehydrogenation process according to claim 11, wherein the at least one inert solvent is selected from the group consisting aromatic hydrocarbons, ethyl acetate, tetrahydrofuran (THF), 2-methyltetrahydrofuran and 1, 4-dioxane.

13. The dehydrogenation process according to claim 2, wherein the process is carried out at a temperature of from 0° C.-150° C.

14. The dehydrogenation process according to claim 7, wherein the process is carried out at a temperature of from 6° C.-150° C.

* * * * *